(12) United States Patent
Kishida

(10) Patent No.: US 8,820,932 B2
(45) Date of Patent: Sep. 2, 2014

(54) OPHTHALMIC PHOTOGRAPHING APPARATUS AND METHOD OF CONTROLLING THE SAME

(75) Inventor: Nobuyoshi Kishida, Nishitokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/216,746

(22) Filed: Aug. 24, 2011

(65) Prior Publication Data

US 2012/0050679 A1 Mar. 1, 2012

(30) Foreign Application Priority Data

Aug. 31, 2010 (JP) ................ 2010-194780

(51) Int. Cl.
*A61B 3/10* (2006.01)
*A61B 3/14* (2006.01)
*A61B 3/00* (2006.01)
*A61B 3/12* (2006.01)

(52) U.S. Cl.
CPC .......... *A61B 3/14* (2013.01); *A61B 3/0008* (2013.01); *A61B 3/1225* (2013.01); *A61B 3/12* (2013.01)
USPC .......................................... 351/206; 351/221

(58) Field of Classification Search
USPC .......... 351/205, 206, 209, 210, 221; 600/310, 600/476
See application file for complete search history.

(56) References Cited

U.S. PATENT DOCUMENTS

| | | | |
|---|---|---|---|
| 4,690,525 A | 9/1987 | Kobayashi et al. | |
| 5,465,123 A | 11/1995 | Iijima | |
| 5,530,494 A | 6/1996 | Ogawa et al. | |
| 5,630,179 A | 5/1997 | Kishida | |
| 5,844,658 A | 12/1998 | Kishida et al. | |
| 6,244,710 B1 | 6/2001 | Ogawa | |
| 6,324,420 B1 | 11/2001 | Kishida et al. | |
| 6,337,993 B1 | 1/2002 | Kishida et al. | |
| 6,834,202 B2 | 12/2004 | Ono | |
| 7,438,413 B2 | 10/2008 | Kashiwagi et al. | |
| 2006/0077344 A1 | 4/2006 | Kashiwagi et al. | |

FOREIGN PATENT DOCUMENTS

| | | |
|---|---|---|
| JP | 60-137347 A | 7/1985 |
| JP | 61-203937 A | 9/1986 |
| JP | 02-237536 A | 9/1990 |
| JP | 03-114434 A | 5/1991 |
| JP | 04-150831 A | 5/1992 |
| JP | 05-038330 A | 2/1993 |
| JP | 05-095905 A | 4/1993 |
| JP | 05-192299 A | 8/1993 |
| JP | 07-171110 A | 7/1995 |
| JP | 08-033612 A | 2/1996 |
| JP | 09-215662 A | 8/1997 |
| JP | 11-235319 A | 8/1999 |
| JP | 11-238129 A | 8/1999 |
| JP | 2000-107133 A | 4/2000 |
| JP | 2000-197608 A | 7/2000 |
| JP | 2001-258852 A | 9/2001 |
| JP | 2003-010134 A | 1/2003 |
| JP | 2005-261447 A | 9/2005 |
| JP | 2005-261449 A | 9/2005 |
| JP | 2005-270152 A | 10/2005 |
| JP | 2005-279154 A | 10/2005 |
| JP | 2006-122647 A | 5/2006 |

*Primary Examiner* — Mahidere Sahle

(74) *Attorney, Agent, or Firm* — Fitzpatrick, Cella, Harper & Scinto

(57) ABSTRACT

An ophthalmic photographing apparatus or method receives light returned from an eye to be examined, calculates a plurality of temporally continuous photometric values based on a light receiving result in the receiving, and determines whether or not the eye is to be photographed, based on the plurality of calculated photometric values.

16 Claims, 9 Drawing Sheets

OPHTHALMIC PHOTOGRAPHING APPARATUS AND METHOD OF CONTROLLING THE SAME

BACKGROUND OF THE INVENTION

1. Field of the Invention

The present invention relates to an ophthalmic photographing apparatus that is used, for example, in an ophthalmic clinic and for a group medical examination and records an image while observing an eye to be examined, a method of controlling the same, and a program.

2. Description of the Related Art

Among ophthalmic photographing apparatuses, fundus cameras that photograph a fundus of an eye to be examined have widely been known. Among the fundus cameras, non-mydriatic fundus cameras have been well known that use near-infrared light, with which the eye does not feel glaringness during observation, and illuminate the fundus of the eye with visible light at the moment of taking a still image and thus photograph the fundus of the eye.

As described in Japanese Patent Application Laid-Open No. H04-150831, the non-mydriatic fundus camera acquires fundus reflectance of an eye to be examined on observation using a dedicated illumination light and a sensor and thereby evaluates brightness of a subject (hereinafter, "photometry"). The camera can automatically determine the optimal amount of light for photographing (light-control) using a value acquired by photometry (hereinafter, "photometric value") and acquire a still image of the fundus of the eye with the optimal brightness.

An operation for photographing an eye to be examined when an apparatus is not in a state capable of photographing causes problems of imposing a load of rephotographing on the eye and wearing of the apparatus. In order to solve the problems, an ophthalmic photographing apparatus disclosed in Japanese Patent Application Laid-Open No. H11-235319 adopts a configuration of prohibiting photographing during a status incapable of recording.

An ophthalmic apparatus disclosed in Japanese Patent Application Laid-Open No. H09-215662 prohibits photographing when a status of alignment with the eye is inappropriate, thereby preventing unnecessary photographing (or measurement).

In recent years, since digitalization is facilitated, a digital camera of a generally used single-lens reflex camera type is adopted as a photographing camera of the fundus camera. This adoption is because the digital camera allows remote photographing from the fundus camera, has high compatibility with a conventional film type camera and further has resolution sufficient for an ophthalmic diagnostic image.

In particular, recently, a function (hereinafter, "live view function") of utilizing a sensor of a digital camera of a single-lens reflex type not only for recording a still image but also for observing and recording a moving image, has been added. This function allows photographing without viewing a viewfinder, thereby leading to an advantage of improving flexibility in the photographing angle. In recent years, inventions using the live view function on observation when attaining alignment and adjusting the focus, have been proposed.

SUMMARY OF THE INVENTION

However, even if light is controlled by a light source other than an observation light source as disclosed in Japanese Patent Application Laid-Open No. H04-150831, the photometric values vary due to adverse effects of positional relationship between the eye and the apparatus and variation in focusing status. Because the photometric values thus vary, an amount of light for photographing cannot be optimized. Further, the fundus camera internally includes an illumination light and a sensor dedicated for light control. Accordingly, the camera is upsized and become expensive.

An ophthalmic apparatus disclosed in Japanese Patent Application Laid-Open No. H09-215662 detects that a status capable of measurement is attained and thereby automatically measures a prescribed part of the eye where measurement causes no problem. However, in an apparatus, such as a fundus camera, with which an operator takes an image according to an operation by the operator after determining an area to be photographed, it is difficult for the apparatus to determine the status capable of photographing. For instance, if the apparatus automatically takes an image according to an operation distance with the eye and a focusing status, an area of the eye out of the intention of the operator might be photographed, thus causing a problem of taking unnecessary images.

The present invention has been made in view of the above problems, and provides an ophthalmic photographing apparatus capable of preventing unnecessary photographing while minimizing adverse effects owing to the positional relationship between the eye and the apparatus and variation in the focusing status.

In order to solve the above problems, the present invention provides with an ophthalmic photographing apparatus, comprising: a light receiving unit that receives light returned from an eye to be examined; a calculation unit that calculates a plurality of temporally continuous photometric values based on a light receiving result from the light receiving unit; and a determination unit that determines whether or not the eye is to be photographed, based on the plurality of photometric values calculated by the calculation unit.

The present invention can prevent unnecessary photographing while minimizing adverse effects owing to the positional relationship between the eye and the apparatus and variation in the focusing status.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

The following embodiments will be described employing a fundus camera as an ophthalmic photographing apparatus.

First Embodiment

Figure 1:
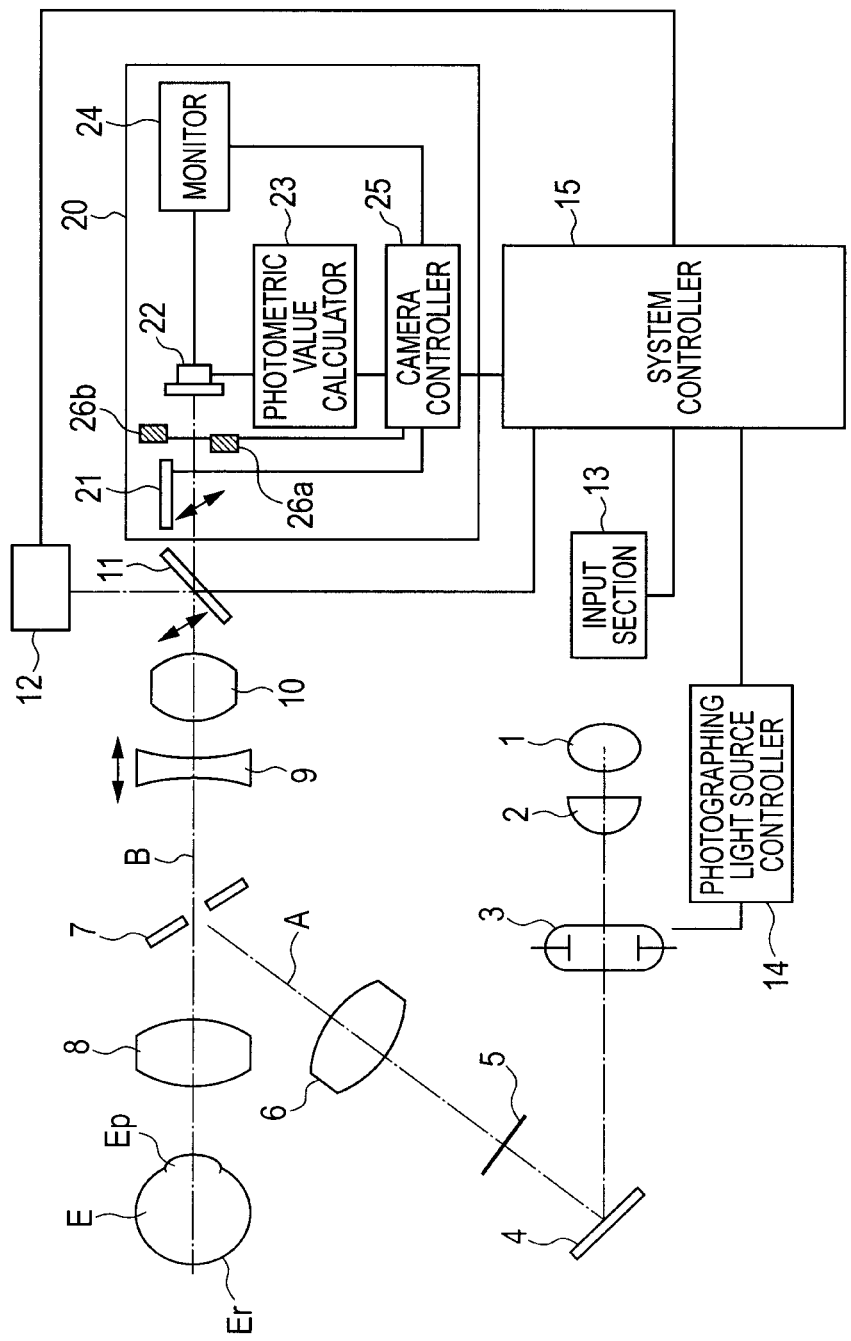
FIG. 1 is a diagram illustrating a configuration of a non-mydriatic fundus camera according to a first embodiment.

FIG. 1 is a diagram illustrating a configuration of a fundus camera according to this embodiment. A non-mydriatic fundus camera is employed as a fundus camera.

In the fundus camera there are sequentially arranged a condenser lens 2, a photographing light source 3, a mirror 4, a diaphragm 5 including an annular opening, a relay lens 6 and a perforated mirror 7 on an optical path from an observation light source 1 to an objective lens 8. These elements configure a fundus illumination optical system A. There are arranged a focusing lens 9, a photographing lens 10, a flip-up mirror 11 in the fundus camera on an optical path in a passing-through direction of the perforated mirror 7. These elements configure an ocular fundus photographing optical system B reaching an imaging element 22 included in a photographing camera 20.

In the reflection direction of the flip-up mirror 11, an internal ocular fixation light 12 is configured. In this light 12, light emitting elements, such as LED, for guiding ocular fixation of an eye E to be examined are systematically arranged. Here, the observation light source 1 is an LED light source emitting infrared light. The flip-up mirror 11 lets infrared light pass but reflects visible light.

Although illustration is omitted, an LED light source for an alignment indicator and a light-emitting end of a light guide guiding a light flux therefrom are arranged in front of the perforated mirror 7. These elements configure an alignment indicator projection system that projects the alignment indicator on a cornea surface of the eye E. Although illustration is omitted likewise, the ocular fundus optical system A includes a focusing indicator projection system that projects a focusing indicator on the fundus Er of the eye E. The alignment indicator projection system and the focusing indicator projection system are configurations important for the fundus camera, but unnecessary for describing characteristics of this embodiment. Accordingly, detailed description thereof is omitted.

The fundus camera further includes a photographing light source controller 14 for controlling the photographing light source 3, and an input section 13 including a photographing start switch for taking a still image of the fundus Er of the eye E. The controller 14 and the input section 13 are connected to a system controller 15 for overall control of the fundus camera.

Next, a configuration in the photographing camera 20 will be described. The photographing camera 20 of this embodiment is a digital camera of a single-lens reflex type, and is a part of the configuration of the aforementioned fundus camera. The photographing camera 20 has a detachable configuration.

The photographing camera 20 includes various functional sections. However, FIG. 1 only illustrates parts necessary to describe the characteristics of this embodiment.

As illustrated in FIG. 1, the photographing camera 20 includes a photographing camera controller 25 for overall control of the photographing camera 20, an imaging element 22, a photometric value calculator 23 calculating a photometric value on an output from the imaging element 22, and a moving image observation monitor 24, such as an LCD. The photographing camera 20 further includes, in front of the imaging element 22, a flip-up mirror 21 in the photographing camera 20, and front and rear curtains 26a and 26b as shutter curtains.

The photographing camera controller 25 is connected to the flip-up mirror 21, the front and rear curtains 26a and 26b, the photometric value calculator 23 and the moving image observation monitor 24, performs overall control of the photographing camera 20 and is further connected to the system controller 15 by an electric contact.

Next, operations of each sections of the fundus camera will be described together with operations by an operator. First, the operation on alignment of the fundus camera will be described.

A flux of infrared light emitted from the observation light source 1 passes through the condenser lens 2 and the photographing light source 3 and is reflected by the mirror 4. The light reflected by the mirror 4 passes through the diaphragm 5, which includes the annular opening, and the relay lens 6, is reflected by a periphery of the perforated mirror 7, passes through the objective lens 8 and the pupil Ep of the eye E and thereby illuminates the fundus Er of the eye with infrared light. Infrared light reflected by the fundus Er of the eye, having been illuminated with infrared light, passes through the pupil Ep of the eye E, the objective lens 8 and a perforation of the perforated mirror 7, transmits through the focusing lens 9, the photographing lens 10 and the flip-up mirror 11, which reflects visual light but lets infrared light pass, and forms an image on the imaging element 22.

Thus, the infrared light emitted from the observation light source 1 is reflected by the fundus Er of the eye and subsequently forms the image on the imaging element 22, thereby being displayed as moving image on the moving image observation monitor 24. A status in which such a subject image formed on the imaging element 22 is displayed on the moving image observation monitor 24 in real time is referred to as a live view status in the photographing camera 20.

Figure 2:
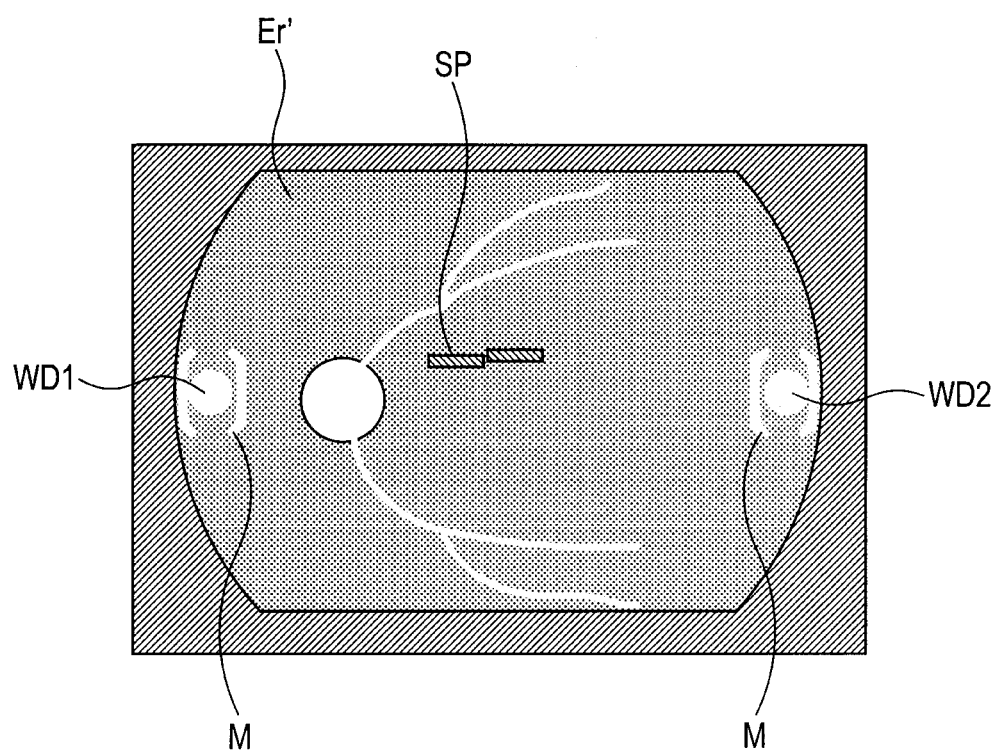
FIG. 2 is a diagram illustrating an observation status according to the first embodiment.

On the other hand, light emitted from the alignment indicator projection system and the focusing indicator projection system are reflected by the fundus Er of the eye and the cornea surface, respectively, and formed on the imaging element 22. FIG. 2 illustrates a status of displaying the alignment indicator, the focusing indicator and the fundus Er of the eye on the moving image observation monitor 24. As illustrated in FIG. 2, alignment indicators WD1 and WD2 and a focusing indicator SP can be observed on the moving image observation monitor 24 together with an observation image Er' of the fundus Er of the eye. The operator aligns the eye E and the fundus camera with each other such that the alignment indicators WD1 and WD2 are in alignment positions M and the focusing indicator SP forms a horizontal line, and focuses the fundus Er of the eye.

As described above, the reason that the light reflected by the fundus Er of the eye including the alignment indicator and the focusing indicator can be guided onto the imaging element 22 is that, during observation, the flip-up mirror 21 is retracted from the ocular fundus photographing optical system B and the front and rear curtains 26a and 26b are in open statuses.

In this status, the photometric value calculator can calculate a photometric value of an observation image formed on the imaging element 22. A process by the photometric value calculator 23 calculating the photometric value thus quantifies brightness of the observation image. More specifically, if the fundus reflectance is low, the photometric value is also low. If the reflectance is high, the photometric value is also high. The process of calculating the photometric value is substantially identical to a process of calculating a fundus reflectance of the eye.

Thus, the operator aligns the eye E and the fundus camera with each other using the moving image observation monitor 24 of the photographing camera 20, and focuses the fundus Er of the eye, thereby allowing the eye E to be aligned. At this time, the photometric value calculator 23 calculates the photometric value of the observation image formed on the imaging element 22. That is, the photographing camera 20 meters the observation image while aligning by the operator.

In a status without using the live view function of the photographing camera 20, the flip-up mirror 21 is disposed in the ocular fundus photographing optical system B, and the front curtain 26a is in a light-shielding status. That is, in the status without using the live view function, the reflected light from the alignment indicator, the focusing indicator and the fundus Er of the eye is not guided onto the imaging element 22. In this case, the observation image is not formed on the imaging element 22. Accordingly, the photometric value calculator 23 cannot calculate the photometric value.

Next, referring to FIGS. 3, 4, 5 and 6, a photographing control method using the photometric value on observation by the fundus camera will be described.

Figure 3:
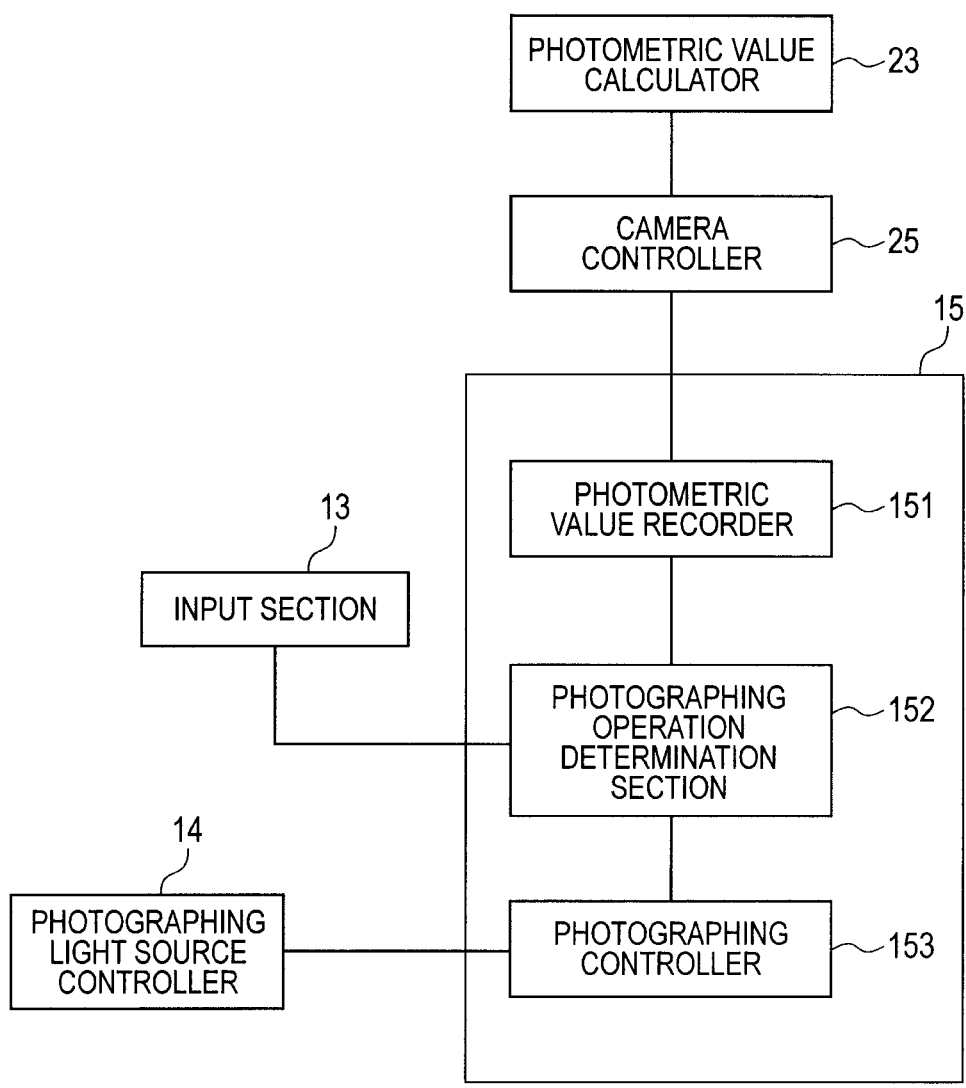
FIG. 3 is a diagram of a configuration of a system controller according to the first embodiment.

First, referring to FIG. 3, a functional configuration of the system controller 15 of the fundus camera will be described.

The system controller 15 includes a photometric value recorder 151 for recording photometric values, a photographing operation determination section 152 for determining whether to perform a photographing operation from photometric values or not, and a photographing controller 153 for executing the photographing operation.

The photographing camera controller 25 notifies the photometric value recorder 151 of the photometric value calculated by the photometric value calculator 23 via an electric contact. The photometric value recorder 151 at least includes a memory, and temporally continuously records the notified photometric values. More specifically, the photometric value recorder 151 records the notified time or order and the photometric value in a manner corresponding to each other.

The photographing operation determination section 152 determines whether to perform photographing or not responsive to a photographing operation via the photographing start switch of input section 13 by the operator based on the photometric values temporally continuously recorded in the photometric value recorder 151. At the same time, the photographing operation determination section 152 outputs a photographing execution instruction to the photographing controller 153 when photographing can be executed.

Next, photographing control using the photometric values on observation by the fundus camera will be described more specifically with reference to flowcharts in FIGS. 4, 5 and 6.

Figure 4:
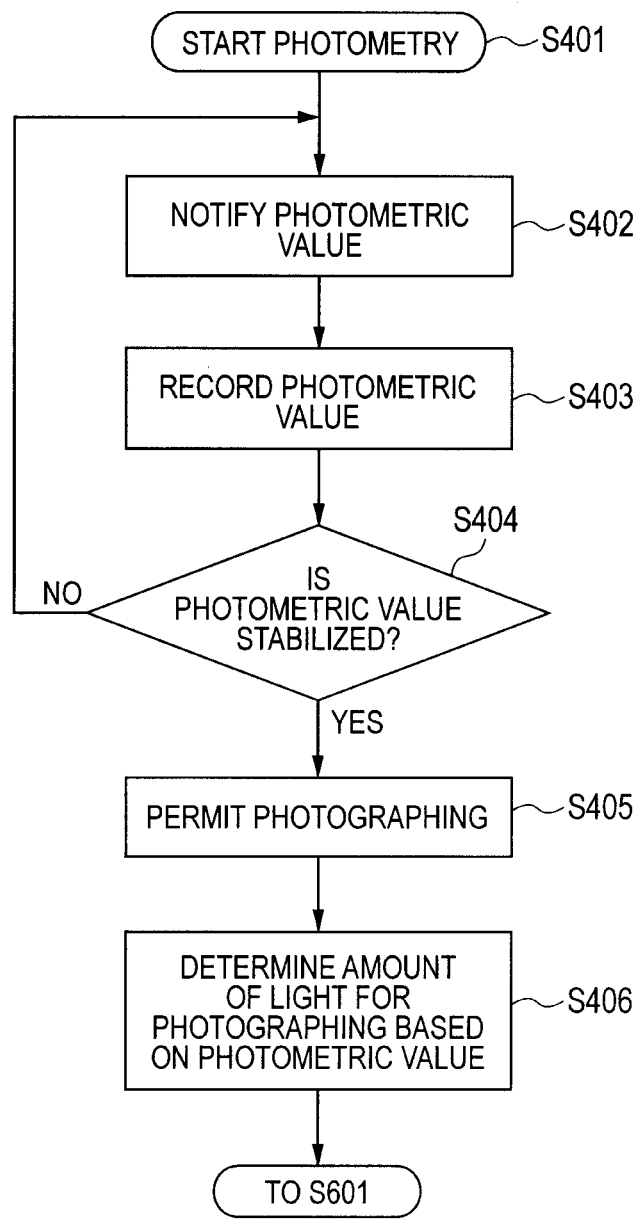
FIG. 4 is a flowchart illustrating a process of measuring light according to the first embodiment.
Figure 5:
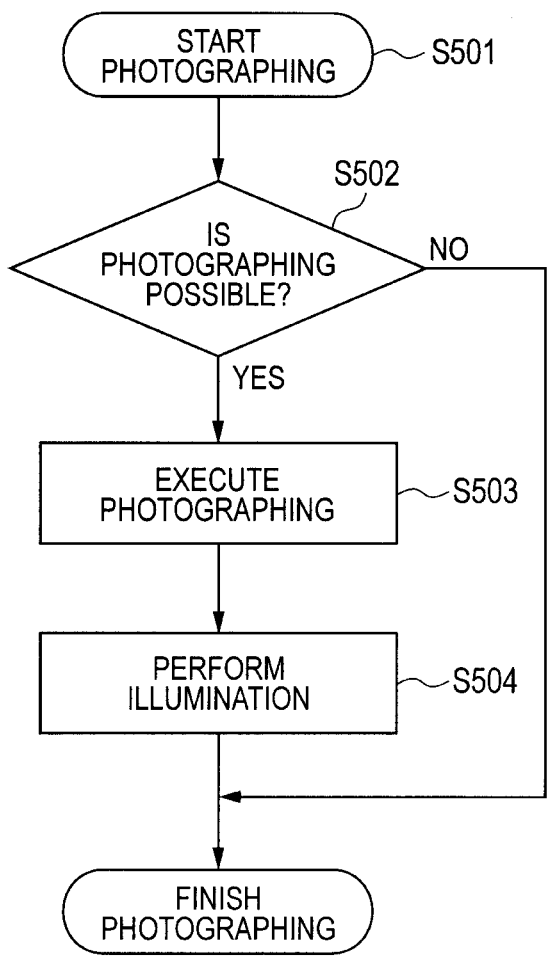
FIG. 5 is a flowchart illustrating a photographing process according to the first embodiment.

First, referring to the flowchart in FIG. 4, a method of determining whether to permit the photographing operation or not is described.

In step S401, the photometric value calculator 23 calculates the photometric value from the observation image captured by the imaging element 22.

In step S402, the photographing camera controller 25 notifies the photometric value recorder 151 included in the system controller 15 of the photometric value calculated by the photometric value calculator 23.

In step S403, the photometric value recorder 151 temporally continuously records the notified photometric value. At this time, the photometric value recorder 151 records the notified photometric value and time or order in a manner corresponding to each other.

In step S404, the photographing operation determination section 152 determines whether the photometric values are stabilized or not based on temporally continuous photometric values recorded in the photometric value recorder 151. The determination of whether the photometric value is stabilized or not is made based on whether the continuous photometric values fall within a prescribed range or not. A method of determining stabilization of the photometric values will be described later with reference to FIG. 7.

In step S404, it is determined that the photometric value is stabilized, the processing proceeds to step S405, and the photographing operation determination section 152 permits a photographing operation. This operation corresponds to an example of a process by photographing operation permission means. Here, for instance, the photographing operation determination section 152 sets a photographing operation permission flag, and stores this status in a memory.

Subsequently, in step S406, the photographing controller 153 determines the amount of light for photographing using the latest photometric value among the stable photometric values.

On the other hand, in step S404, it is determined that the photometric value is not stabilized, the processing returns to step S402, and processes of steps S402 to S404 are repeated.

That is, the processing does not proceed to step S405 and the photographing operation is not permitted, until the photographing operation determination section 152 determines that the photometric values are stabilized in step S404.

Next, referring to the flowchart illustrated in FIG. 5, a photographing execution process will be described.

In step S501, in parallel with the determination of whether to permit the photographing operation or not in the flowchart of FIG. 4, the photographing operation determination section 152 detects an operation of starting photographing via the photographing start switch of the input section 13.

In step S502, the photographing operation determination section 152 determines whether photographing is possible or not. More specifically, the photographing operation determination section 152 determines whether the photographing operation in step S405 has been permitted or not according to the determination of step S404 shown in the flowchart in FIG. 4. Here, for instance, the photographing operation determination section 152 determines whether the photographing operation permission flag of the memory is set or not. If the photographing operation permission flag is set, it is determined that the photographing is possible.

If the photographing is possible, the processing proceeds to step S503 and the photographing operation determination section 152 outputs a photographing execution instruction to the photographing controller 153. The photographing controller 153 starts the photographing operation according to the photographing execution instruction.

Next, in step S504, the photographing light source controller 14 performs illuminating operation via the photographing light source 3 based on the amount of light for photographing determined in step S406 illustrated in the flowchart of FIG. 4. At this time, the photographing camera controller 25 acquires a taken image of the eye formed on the imaging element 22 in synchronization with the timing of the illuminating operation in cooperation with the photographing light source controller 14.

On the other hand, if it is determined that photographing is impossible in step S502, the photographing controller 153 does not start the photographing operation and finishes the photographing.

It is thus determined whether the photographing operation is permitted or not based on whether the photometric values are stabilized or not in the aforementioned step S404. Accordingly, in a case where the photometric value is not stabilized owing to variation in the positional relationship between the eye and the apparatus and variation in the focusing status, it is not required to perform unnecessary photographing.

Next, referring to the flowchart of FIG. 6, the photometric value processing and the photographing operation after the photographing operation is permitted will be described.

Step S601 is a process subsequent to step S406 illustrated in the flowchart of FIG. 4. More specifically, the processing of the flowchart illustrated in FIG. 4 is of a status in which it has been determined that the photometric value is stabilized in step S404, the photographing operation has once permitted and the amount of light for photographing has been determined.

Even after the photographing is permitted, processes of step S601 (analogous to step S401), step S602 (analogous to step S402) and step S603 (analogous to step S403) are executed on the photometric value.

Subsequently, in step S604, the photographing operation determination section 152 executes a process of determining whether the photometric value is normal or not. Here, the determination of whether the photometric value is normal or not is made based on whether the absolute value of the difference between the notified measured value at the present time and the latest recorded measured value falls within a prescribed range or not. For instance, blinking of the eye can be considered as a case of an abnormal photometric value. A specific determination method in step S604 will be described later with reference to FIG. 7.

If the photometric value is normal, step S605 (analogous to step S406) is executed and the photographing controller 153 determines the amount of light for photographing based on the photometric value.

On the other hand, if the photographing operation determination section 152 determines that the photometric value is not normal but is abnormal in step S604, the processing returns to step S602. Accordingly, the new amount of light for photographing based on the photometric value is not determined until the photometric value becomes normal. In other words, after the photographing has once been permitted, the amount of light for photographing based on the normal photometric value is always determined. Accordingly, in step S501 illustrated in the flowchart of FIG. 5, if the photographing start switch operation is received from the input section 13, the photographing and illuminating operations in steps S503 and S504 are executed according to the determination in step S502.

Figure 6:
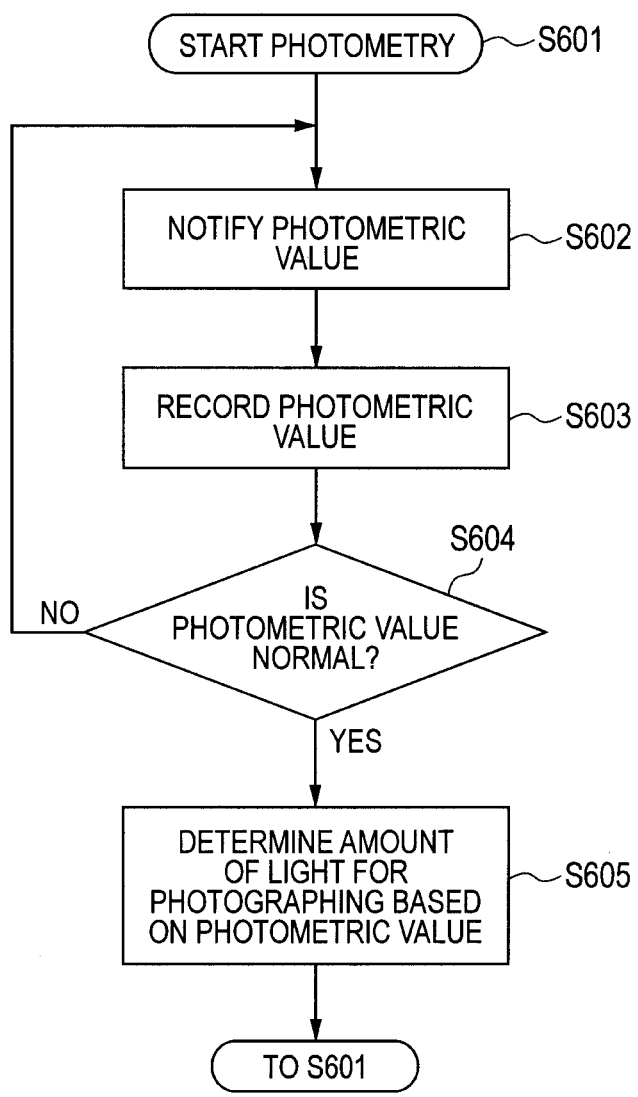
FIG. 6 is a flowchart illustrating abnormal photometric value processing according to the first embodiment.

Thus, in the flowchart of FIG. 6, in the status where the photographing operation has once been permitted, even if the photometric value becomes abnormal, the abnormal photometric value is not reflected and the status capable of photographing is maintained. More specifically, in step S604, even in a case where the photometric value abruptly varies owing to blinking of the eye and the photometric value becomes abnormal, only the abnormal photometric value is ignored and the photographing operation is not prohibited. Accordingly, an image with the optimal brightness can be taken without adverse effects of blinking of the eye.

Next, referring to FIG. 7, a process of determining whether the photometric value in step S404 is stabilized or not and a process of determining whether the photometric value in step S604 is normal or not will be described.

Figure 7:
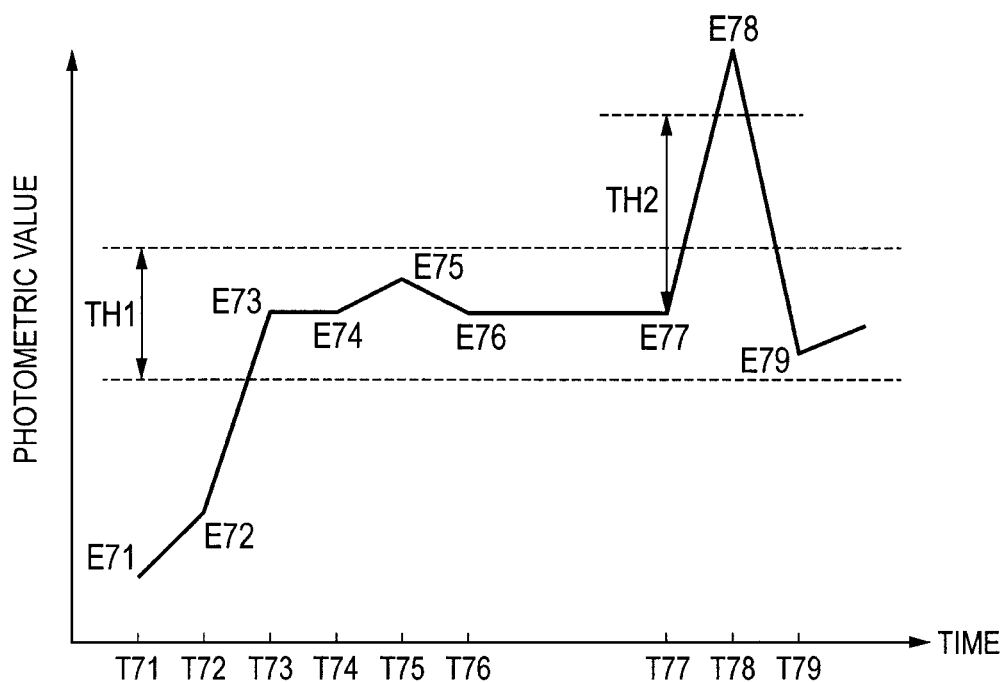
FIG. 7 is a diagram illustrating variation in photometric value according to the first embodiment.

Photometric values E71 to E79 illustrated in FIG. 7 are examples of photometric values calculated by the photometric value calculator 23 and notified by the photographing camera controller 25 to the photometric value recorder 151.

The photometric values E71 to E79 are notified on times T71 to T79, respectively. The latest photometric value in FIG. 7 is the photometric value E79 notified on the time T79. The photometric value E71 notified on the time T71 is the first notified photometric value. According to a range TH1, the photometric value is determined to be stabilized in FIG. 7. According to a range TH2, the photometric value is determined to be abnormal.

First, a process of determining whether the photometric value in step S404 is stabilized or not will be described.

The two photometric values E71 and E72 are out of the range TH1. A case of acquiring such photometric values is a case where the fundus of the eye is not appropriately observed because the alignment is in the middle thereof or a case where ocular fixation of the eye is not stabilized.

On the other hand, for instance, the photometric values E73, E74 and E75 continuously fall within the range TH1. A case of acquiring such photometric values is a case where the alignment is completed and the fundus of the eye can appropriately be observed.

In step S404, in a case where, as with the photometric values recorded by the photometric value recorder 151, for instance, from the two continuous photometric values E71 and E72 to the photometric values E73 to E75, three photometric values continuously fall within the range TH1, the photographing operation determination section 152 determines that the photometric value is stabilized. That is, the photographing operation determination section 152 permits the photographing operation on the time T75, on which the third photometric value E75 is notified among the three photometric values E73 to E75 continuous in the range TH1.

This embodiment describes the case of permitting the photographing operation in a case where continuous three photometric values fall within the range TH1. However, cases are not limited to three continuous photometric values. For instance, in a case where two continuous photometric values or at least four continuous photometric values fall within the range TH1, the photographing operation may be permitted. The range TH1 of the photometric values, according to which the photometric value is determined to be stabilized, becomes effective in a case of adopting a range of ±0.3 Ev in units of Ev (exposure value), a numerical value indicating a brightness of exposure, where the difference of brightness is distinct.

In this embodiment, photometry is performed with fixed intervals of the times T71 to T79 (e.g., 1/30 sec.×6 times=ca 200 ms) in synchronization with the period of the refresh timing (1/30 sec.) of the observation image, thereby allowing acquisition of a temporal variation in the photometric value. It is a matter of course that the variation of the photometric values can be observed in detail by reducing the intervals of the times T71 to T79.

Next, a process of determining whether the photometric value in step S604 is normal or not will be described. In step S604, the photographing is permitted on the aforementioned time T75, and subsequently, the photometric values up to E77 fall within the range TH1. Next, the absolute value of the difference between the photometric value E78 notified on the time T78 and the immediately previous photometric value E77 exceeds the range TH2, according to which the photometric value is determined to be abnormal. Here, the range TH2 is, for instance, ±1.0 Ev in units of Ev.

In a case of acquiring such a photometric value, blinking of the eye can be considered. Accordingly, the photometric value E78 is not reflected in the amount of light for photographing. That is, the photometric value to be reflected in the amount of light for photographing is the photometric value E77 immediately previous to the abnormal photometric value E78. Under the adverse effects owing to blinking of the eye, as illustrated in FIG. 7, the photometric value E79 becomes a value close to the photometric value E77.

As described above, after the photographing operation has once been permitted, the photographing operation is not prohibited even if the photometric value becomes abnormal. This is because the photometric value is a value of the previous observation image. That is, the abnormal photometric value E78 illustrated in FIG. 7 is a photometric value of an observation image before the time T78, for instance around the time T77. That is, at the time T78 when the photometric value E78 is notified, the observation image is of the next photometric value E79.

Thus, if the photographing operation is prohibited with the abnormal photometric value E78, the photographing operation is prohibited during the observation image with the photometric value E79 capable of observing the fundus of the eye is observed. Accordingly, the operator misses the timing of photographing. Further, this prohibition gives the operator an uncomfortable sense of operation according to which the photographing starting operation cannot be accepted when photographing is desired. Further, such photographing is incapable as the operator instructs the subject to blink immediately before the photographing in order to avoid an adverse effect of tears.

In this embodiment, in order not to cause such a problem, the processing is executed on the abnormal photometric value E78 so as not to prohibit the photographing, not to change the photometric value to be reflected in the amount of light for photographing, and not to determine the amount of light for photographing in which the abnormal photometric value E78 is reflected. Note that, although the range TH2 according to which the photometric value is determined to be abnormal is set to ±1.0 Ev in units of Ev, another value may be adopted.

Further, in this embodiment, the photographing is not prohibited when blinking. However, combination with a conventional technique improving time from the photographing starting operation to light-emission of the photographing light source can prevent a photographing failure.

Second Embodiment

Figure 8:
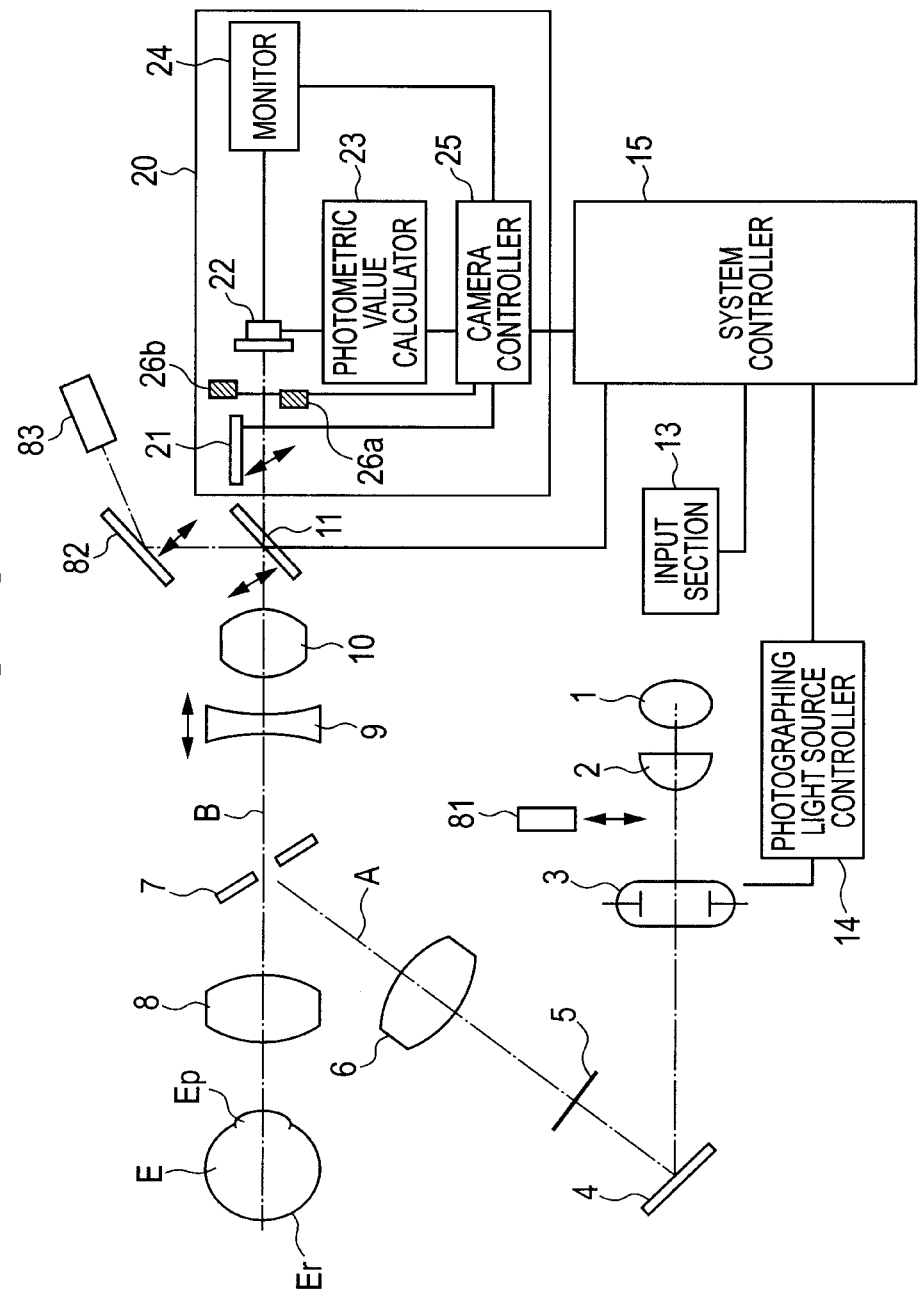
FIG. 8 is a diagram illustrating a configuration of a mydriatic fundus camera according to a second embodiment.

A second embodiment describes a case of application to a mydriatic fundus camera. Referring to FIG. 8, a configuration of a fundus camera according to this embodiment will be described. Configurational elements identical to the elements in the first embodiment are assigned with identical symbols. The description thereof is omitted.

This embodiment adopts a configuration in which an infrared cut filter 81, an extractable reflection mirror and a direct viewfinder 83 are added to the fundus camera of the first embodiment. The infrared cut filter 81 can be inserted and extracted into and from the illumination optical system A, and disposed between the condenser lens 2 and the photographing light source 3. The reflection mirror 82 is disposed above the flip-up mirror 11, and can guide light to the direct viewfinder 83 allowing the operator to observe the eye with visible light. In the second embodiment, instead of the internal ocular fixation light illustrated in FIG. 1, an external ocular fixation light which is not shown is arranged, thereby allowing ocular fixation of the subject to be guided in more detail.

Further, what is different in function from the first embodiment is the observation light source 1. Although the first embodiment adopts the LED emitting infrared light as the observation light source 1, the second embodiment adopts a halogen lamp emitting visible light.

Next, operations and procedures will be described.

In the second embodiment, during observation, the infrared cut filter 81 is detached from the fundus illumination optical system A. A light flux of the visible light emitted from the observation light source 1 passes through the condenser lens 2 and used for irradiation including an infrared component remaining therein. Since elements up to the flip-up mirror 11 are identical to the elements of the first embodiment, the description thereof is hereinafter omitted. The flip-up mirror 11 lets infrared light pass but reflects visible light. Accordingly, the visible light is reflected in the direction of the reflection mirror 82. The light reflected by the reflection mirror 82 can be observed through the direct viewfinder 83. Thus, in contrast to the first embodiment, this embodiment allows aligning the eye E while performing direct view observation using visible light.

The infrared light having passed through the flip-up mirror 11 is photographed as it is by the imaging element 22 of the photographing camera 20. Accordingly, a photometry process analogous to the process of the first embodiment can be performed. The first embodiment adopts the live view function of the photographing camera 20, thereby allowing observation using moving image observation monitor 24. Also in the second embodiment, an analogous manner is adopted, thereby allowing both infrared observation by the photographing camera 20 and visible light observation by the direct viewfinder 83. If display of the moving image observation monitor 24 is turned off, the power can be saved. Further, if a sensor is arranged adjacent to the direct viewfinder 83, a manner of operation is facilitated. According to this manner, display of the moving image observation monitor 24 is turned off only during the operator performs visible light observation.

The configuration described above allows even the mydriatic fundus camera performing visible light observation through the direct viewfinder 83 to exert advantageous effects analogous to the non-mydriatic fundus camera performing infrared observation of the first embodiment. In this embodiment, the reflectance of the fundus of the eye is calculated using an infrared component of the halogen lamp emitting the visible light. Here, if a mirror allowing a part of visible light to pass through is adopted as the flip-up mirror 11, the mechanism inserting and extracting the infrared cut filter 81 can be emitted. Thus, infrared light is not necessarily used as observation light source for calculating the photometric value.

Figure 9:
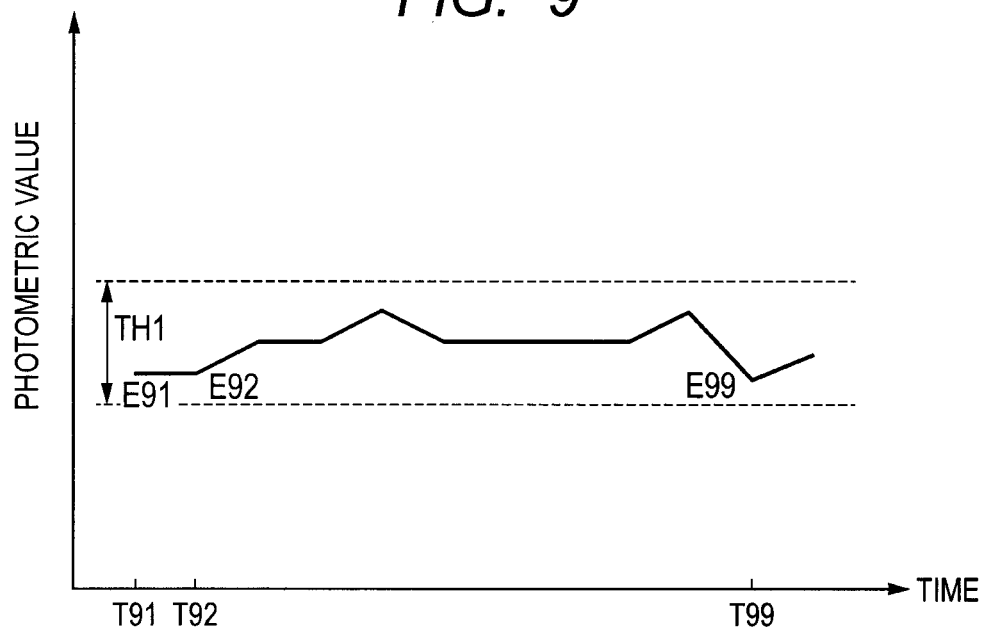
FIG. 9 is a diagram illustrating variation in photometric value during consecutively photographing an identical an eye to be examined according to the second embodiment.

Next, a method that optimally manages the photometric values during consecutively photographing the eye and is specific to the mydriatic fundus camera will be described. FIG. 9 illustrates states of the photometric values on the second photographing in a case of consecutively photographing the photographed eye having been photographed in FIG. 7. The photometric value used for photographing in FIG. 7 is the photometric value E79. A first photometric value E91 in FIG. 9 is substantially identical to the photometric value E79. This is because the status of alignment is hardly changed on the identical eye having once been photographed, thereby the first photometric value in the consecutive photographing to be stably acquired.

Figure 10:
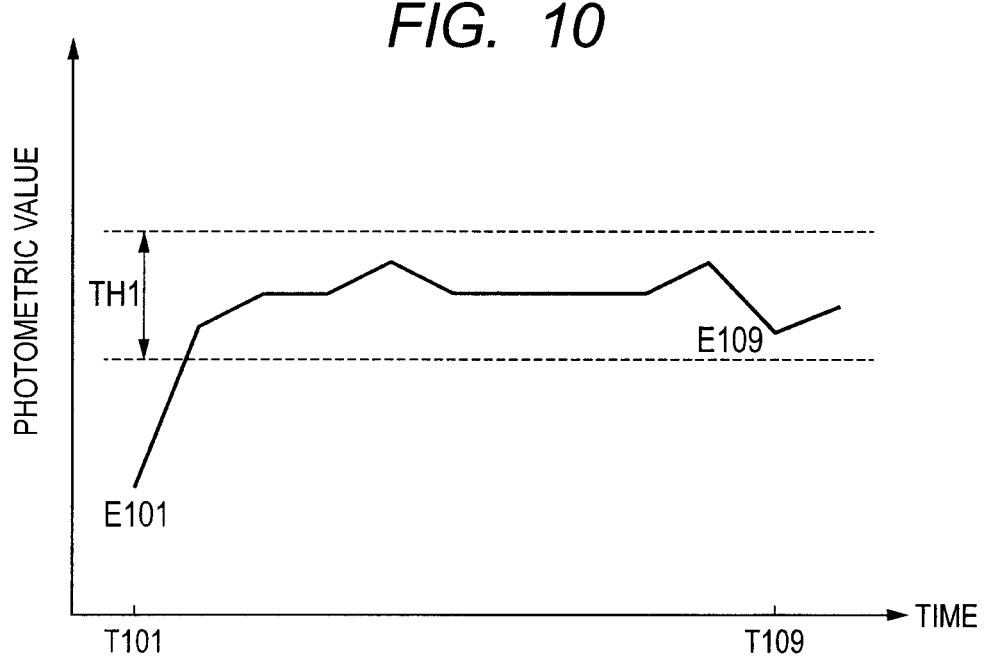
FIG. 10 is a diagram illustrating variation of photometric values during consecutively photographing another eye according to the second embodiment.

FIG. 10 is a diagram illustrating a variation of the photometric values in a case of photographing the eye other than the photographed eye having been photographed in FIG. 7. The photometric value used for photographing in FIG. 7 is the photometric value E79. It can be understood that a first photometric value E101 in FIG. 10 is largely different from the photometric value E109. This is because there is a need for another alignment, and stable photometric values as with the consecutive photographing of the identical eye cannot be acquired. In this case, the photometric value recorder 151 initializes the recorded photometric values so as not to determine the amount of light for photographing based on the recorded photometric value.

Accordingly, when photographing identical eye, the photometric value E79 having been used for photographing and the photometric values E91 and E92 acquired on the times T91 and T92, respectively, are used. Thus, it is regarded that three continuous photometric values within the prescribed range TH1 are acquired, thereby allowing photographing on the time T92.

As described above, in the case of photographing the identical eye, a photographing prohibition period in consecutive photographing is reduced, thereby allowing the apparatus to be excellent in operability.

It can easily be detected whether the identical eye is being photographed or not, by using the detection switch (eye detector) that is arranged at a movable part of the fundus camera and detects which eyes are photographed. Further, if the fundus camera is connected to the personal computer and combined with application software for managing subject information and taken images, it is facilitated to detect that the eye has been changed.

Since the ophthalmic photographing apparatuses of the aforementioned first and second embodiments thus control to record the photometric values and permit the photographing operation using the photometric value. Accordingly, the photographing is prohibited during the photometric value is not stable. Accordingly, the photographing is prohibited if the photometric value is not stable owing to the positional relationship between the eye and the apparatus and the variation of the focusing status. This prohibition can prevent unnecessary photographing from being performed.

The photographing operation is permitted after the photometric value is stabilized. With abrupt variation of the photometric value thereafter due to such as blinking, only this photometric value is ignored but the photographing is not prohibited. Accordingly, without any adverse effect owing to blinking of the eye, the taken image with the optimal brightness can be acquired.

If the eye to be photographed is not changed, the photometric value used in the immediately previous photographing is utilized. This utilization allows the photographing prohibition period in consecutive photographing to be reduced and enables the operability to be improved.

Further, in the photographing camera 20, the element for acquiring the observation image for calculating the photometric value and the element on which the image of the eye to be photographed is formed are the identical element, which is the imaging element 22. That is, the imaging element 22 is shared for photographing and calculating the photometric value. This configuration enables the apparatus to be simplified in comparison with a case of configuring a sensor dedicated for photometry.

Moreover, photometry is performed utilizing the generally used digital camera. This configuration negates the need of a dedicated sensor for controlling light, enables the apparatus to be downsized and allows inexpensive configuration.

Another Embodiment

The present invention may configure a computer as the aforementioned system controller 15. The computer reads a program stored in ROM and executes the program, thereby allowing the processes of flowcharts of FIGS. 4, 5 and 6 to be executed.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-194780, filed Aug. 31, 2010, which is hereby incorporated by reference herein in its entirety.

What is claimed is:

1. An ophthalmic photographing apparatus, comprising:
a light receiving unit configured to receive light returned from an eye to be examined irradiated by light;
an acquiring unit configured to acquire a plurality of temporally continuous photometric values based on the received light; and
a control unit configured to determine whether photography is permitted based on the acquired plurality of temporally continuous photometric values being within a prescribed range, and to output an instruction to start executing a photography operation in response to inputting an instruction to start executing the photography operation in a case where it is determined that photography is permitted.

2. The ophthalmic photographing apparatus according to claim 1, wherein the control unit sets a photographing operation permission flag in a case where the acquired plurality of temporally continuous photometric values are within the prescribed range.

3. The ophthalmic photographing apparatus according to claim 1, further comprising:
a photographing light source; and
a determination unit configured to determine an amount of light of the photographing light source based on at least one of the plurality of temporally continuous photometric values within the prescribed range,
wherein the control unit controls the photographing light source based on the determined amount of light.

4. The ophthalmic photographing apparatus according to claim 1, further comprising a photographing light source, wherein, after the control unit permits the photographing operation, the control unit controls the photographing light source based on one of (i) the plurality of temporally continuous photometric values, (ii) the absolute value of the difference between the one photometric value and (iii) a photometric value immediately previous to the one photometric value being within the prescribed range.

5. The ophthalmic photographing apparatus according to claim 1, further comprising a photographing light source, wherein the light receiving unit includes an imaging element for imaging the eye, and wherein the control unit acquires an image of the eye based on an output of the imaging element after controlling the photographing light source.

6. The ophthalmic photographing apparatus according to claim 1, further comprising a recording unit configured to record the plurality of photometric values, wherein the recording unit initializes the plurality of photometric values in a case where the eye is switched from one of right and left eyes to the other or the subject is replaced.

7. The ophthalmic photographing apparatus according to claim 1, further comprising:
an observation light source configured to observe the eye; and
a photographing light source configured to photograph the eye,
wherein the control unit controls the amount of light from the photographing light source based on the light returned from the eye illuminated with observation light emitted from the observation light source.

8. An ophthalmic photographing method, comprising:
receiving light returned from an eye to be examined irradiated by a light;

acquiring a plurality of temporally continuous photometric values based on the received light; and determining whether photography is permitted based on the acquired plurality of temporally continuous photometric values being within a prescribed range, and outputting an instruction to start executing a photography operation in response to inputting an instruction to start executing the photography operation in a case where it is determined that photography is permitted.

9. A non-transitory computer-readable storage medium storing a computer program that causes a computer to execute an ophthalmic photographing method, the method comprising:

receiving light returned from an eye to be examined irradiated by a light;

acquiring a plurality of temporally continuous photometric values based on the received light; and determining whether photography is permitted based on the acquired plurality of temporally continuous photometric values being within a prescribed range, and outputting an instruction to start executing a photography operation in response to inputting an instruction to start executing the photography operation in a case where it is determined that photography is permitted.

10. The ophthalmic photographing apparatus according to claim 1, further comprising an observation light source, wherein the light receiving unit includes an imaging element for imaging the eye, wherein the control unit acquires an observation image of the eye based on an output of the imaging element, and wherein the acquiring unit acquires the plurality of temporally continuous photometric values based on the observation image.

11. The ophthalmic photographing apparatus according to claim 1, wherein the acquiring unit acquires the plurality of temporally continuous photometric values in periods of refresh timing of an observation image.

12. The ophthalmic photographing apparatus according to claim 2, further comprising a photographing start switch, wherein the control unit determines whether or not the photographing operation permission flag is set in response to an output from the photographing start switch.

13. The ophthalmic photographing apparatus according to claim 1, wherein the control unit completes alignment in a case where the acquired plurality of temporally continuous photometric values are within the prescribed range.

14. An ophthalmic photographing apparatus, comprising:
a photographing light source;
a light receiving unit configured to receive light returned from an eye to be examined irradiated by a light;
an acquiring unit configured to acquire a plurality of temporally continuous photometric values;
a determination unit configured to determine, in a case where the acquired plurality of temporally continuous photometric values are within a prescribed range, an amount of light of the photographing light source based on at least one of the acquired plurality of temporally continuous photometric values within the prescribed range; and
a control unit configured to control, the photographing light source based on the determined amount of light.

15. An ophthalmic photographing method, comprising:
receiving light returned from an eye to be examined irradiated by a light;
acquiring a plurality of temporally continuous photometric values;
determining, in a case where the acquired plurality of temporally continuous photometric values are within a prescribed range, an amount of light of a photographing light source based on at least one of the acquired plurality of temporally continuous photometric values within the prescribed range; and
controlling the photographing light source based on the determined amount of light.

16. A non-transitory computer-readable storage medium storing a computer program that causes a computer to execute an ophthalmic photographing method, the method comprising:

receiving light returned from an eye to be examined irradiated by a light;

acquiring a plurality of temporally continuous photometric values;

determining, in a case where the acquired plurality of temporally continuous photometric values are within a prescribed range, an amount of light of a photographing light source based on at least one of the acquired plurality of temporally continuous photometric values within the prescribed range; and controlling the photographing light source based on the determined amount of light.

* * * * *